«12» United States Patent
Clark

«10» Patent No.: US 11,963,926 B2
«45» Date of Patent: Apr. 23, 2024

«54» SELF-LOCKING COVER FOR DRUG WASTE MANAGEMENT AND SYSTEMS IMPLEMENTING THEREOF

«71» Applicant: Stephen Clark, Jacksonville, FL (US)

«72» Inventor: Stephen Clark, Jacksonville, FL (US)

«*» Notice: Subject to any disclaimer, the term of this patent is extended or adjusted under 35 U.S.C. 154(b) by 208 days.

«21» Appl. No.: 17/489,314

«22» Filed: Sep. 29, 2021

«65» Prior Publication Data

US 2022/0096323 A1 Mar. 31, 2022

Related U.S. Application Data

«60» Provisional application No. 63/084,891, filed on Sep. 29, 2020.

«51» Int. Cl.
| | | |
|---|---|---|
| *G08B 13/14* | (2006.01) |
| *A61J 1/03* | (2023.01) |
| *A61J 1/14* | (2023.01) |
| *A61J 1/16* | (2023.01) |
| *A61J 1/18* | (2023.01) |
| *A61J 1/20* | (2006.01) |
| *B65D 55/02* | (2006.01) |
| *G16H 20/13* | (2018.01) |
| *G16H 40/20* | (2018.01) |
| *G16H 40/63* | (2018.01) |

«52» U.S. Cl.
CPC .......... *A61J 1/1431* (2015.05); *A61J 1/03* (2013.01); *A61J 1/16* (2013.01); *A61J 1/18* (2013.01); *A61J 1/2048* (2015.05); *A61J 1/2096* (2013.01); *B65D 55/02* (2013.01); *G16H 20/13* (2018.01); *G16H 40/20* (2018.01); *G16H 40/63* (2018.01); *A61J 2200/70* (2013.01); *A61J 2200/76* (2013.01)

«58» Field of Classification Search
CPC .... A61J 1/1431; A61J 1/03; A61J 1/16; A61J 1/18; A61J 1/2048; A61J 1/2096; A61J 2200/70; A61J 2200/76; A61J 1/065; B65D 55/02; G16H 20/13; G16H 40/20; G16H 40/63
USPC ....................................... 340/572.1
See application file for complete search history.

«56» References Cited

U.S. PATENT DOCUMENTS

| | | | | |
|---|---|---|---|---|
| 2013/0141236 A1* | 6/2013 | Chu | ............. | G08B 21/24 |
| | | | | 340/539.12 |
| 2015/0020825 A1* | 1/2015 | Galloway | ............. | A24F 40/53 |
| | | | | 340/407.1 |

* cited by examiner

*Primary Examiner* — Tai T Nguyen
«74» *Attorney, Agent, or Firm* — Wilson Dutra, PLLC; Camille A. Wilson

«57» ABSTRACT

The present disclosure relates to systems that rely on a self-locking cover to limit access to narcotics. A self-locking cover may allow for a single access opportunity to a narcotics vial, which may be one or both original vials and waste vials. In some aspects, a self-locking cover may be incorporated into narcotics transportation and tracking mechanisms, which may allow for increased security against tampering or abuse of narcotics, particularly narcotics waste. Self-locking covers may prevent uninhibited and free access to waste narcotics, which may be susceptible to abuse.

8 Claims, 21 Drawing Sheets

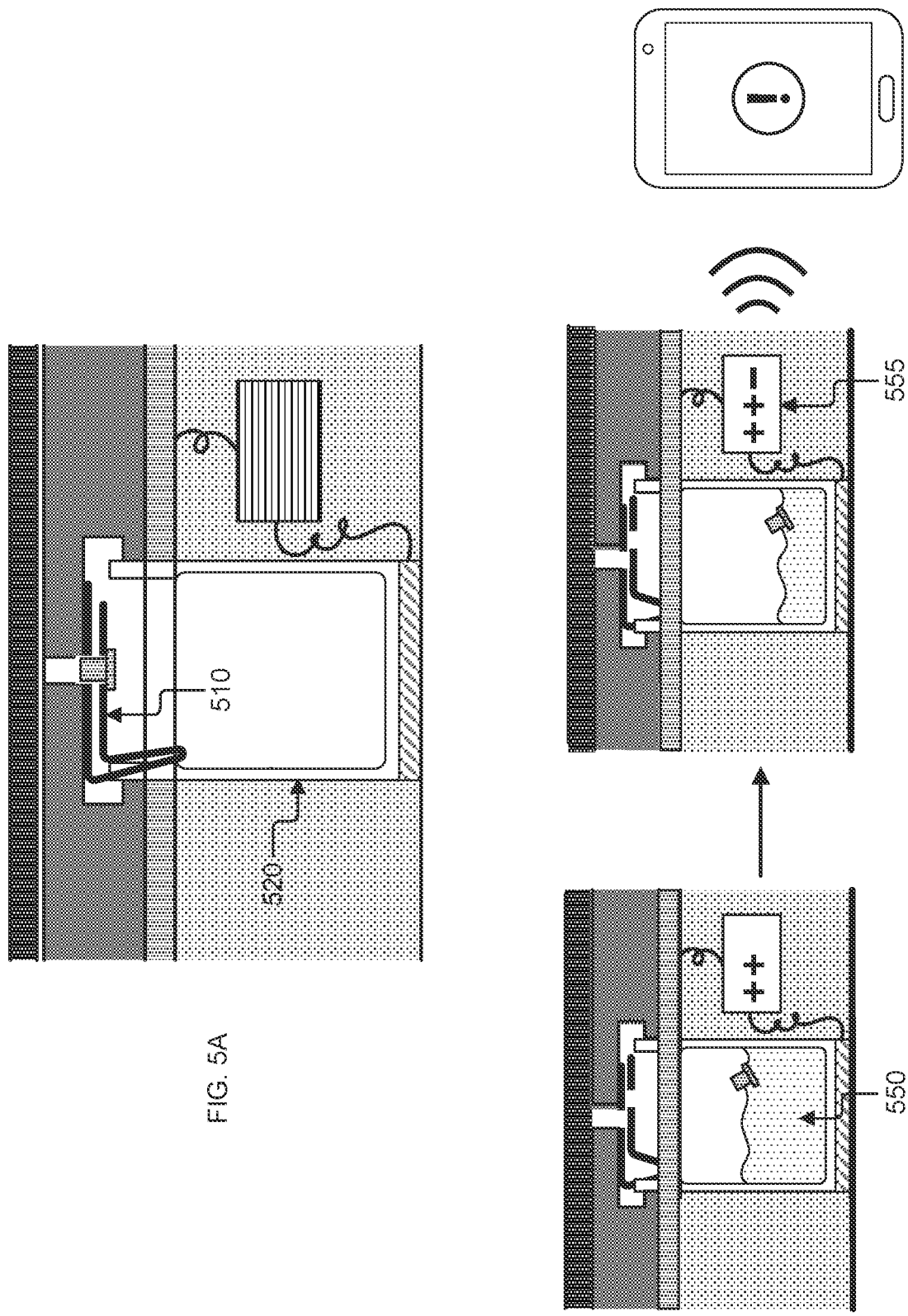

600

600

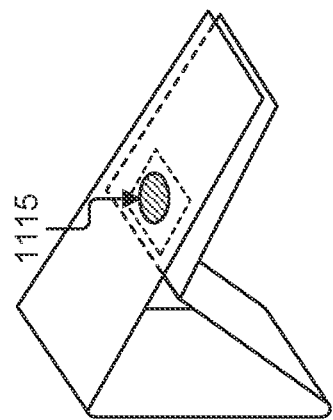
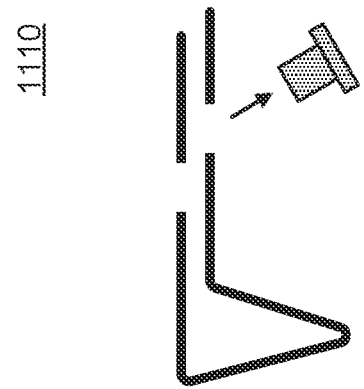
FIG. 11A
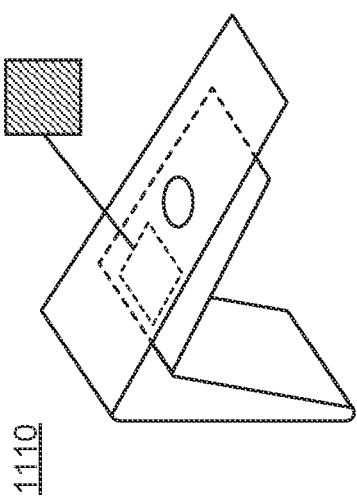
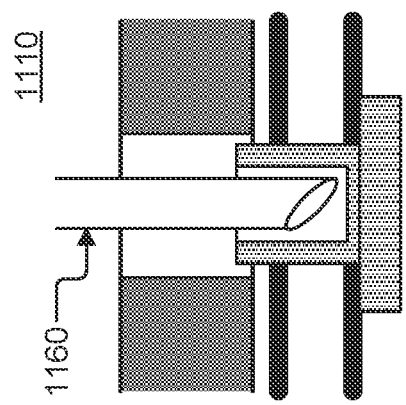
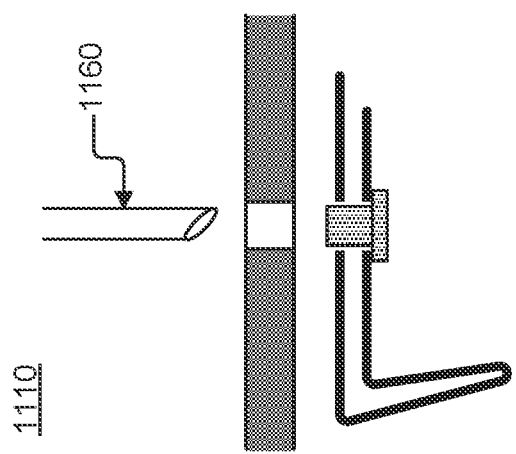
FIG. 11B

FIG. 13A
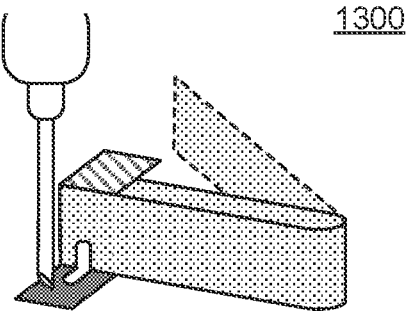
1300
FIG. 13B
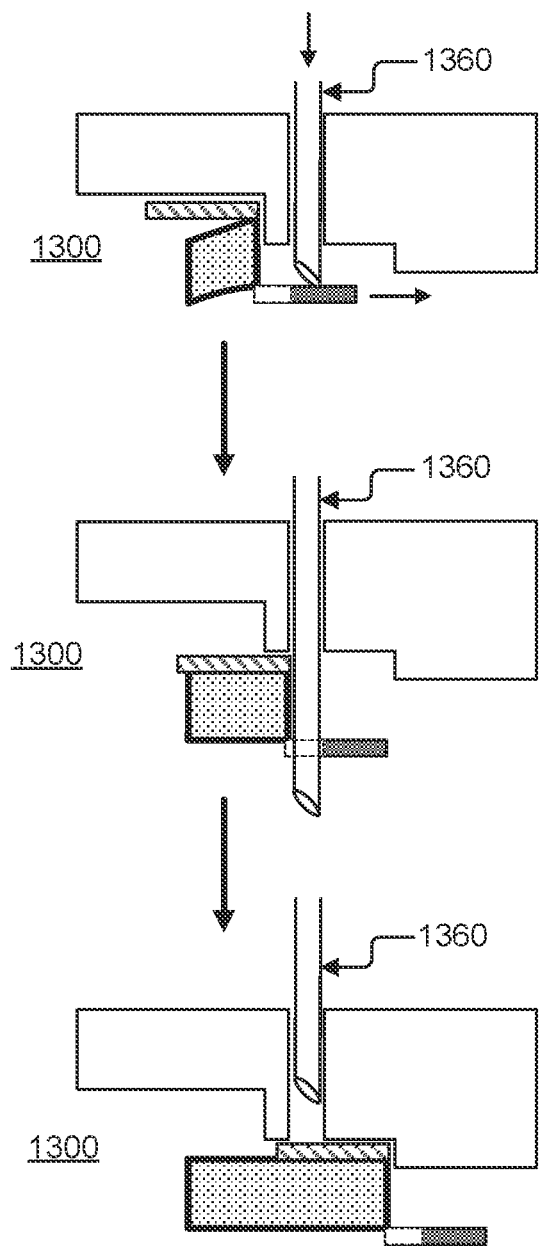
FIG. 13C
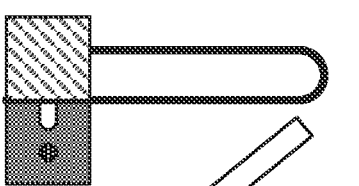
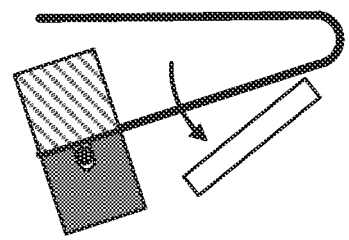
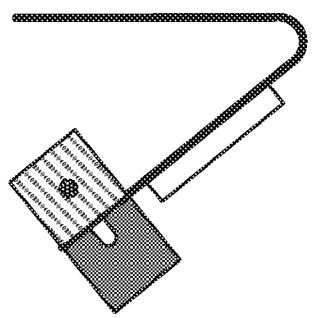

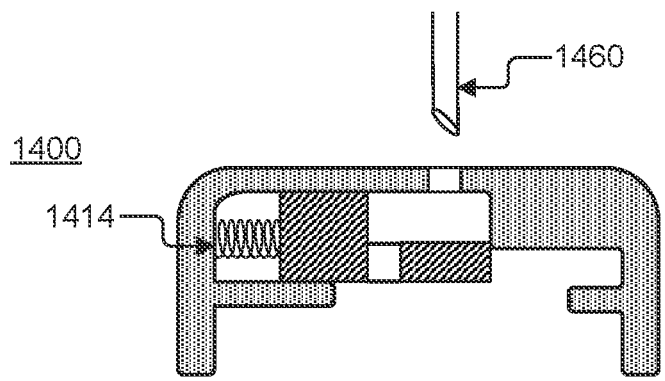
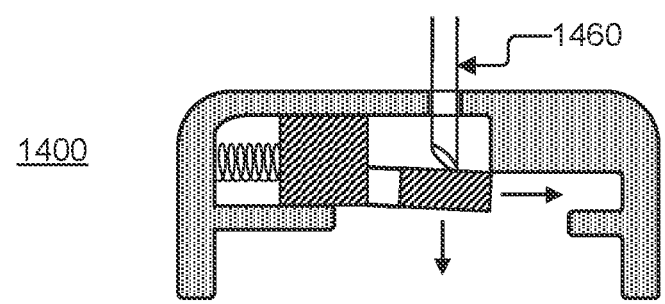
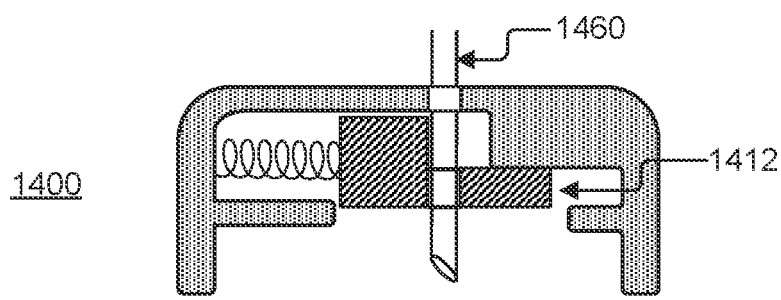
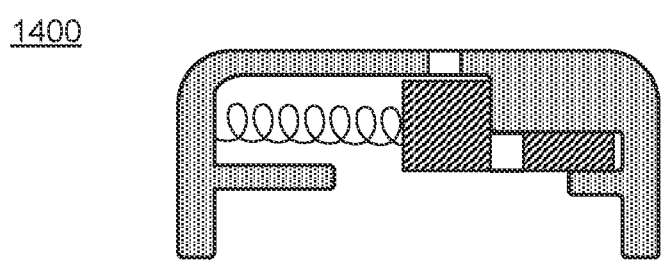
FIG. 14

SELF-LOCKING COVER FOR DRUG WASTE MANAGEMENT AND SYSTEMS IMPLEMENTING THEREOF

CROSS-REFERENCE TO RELATED APPLICATION

This application claims priority to and the full benefit of U.S. Provisional Patent Application Ser. No. 63/084,891, filed Sep. 29, 2020, and titled "SELF-LOCKING COVER FOR DRUG WASTE MANAGEMENT AND SYSTEMS IMPLEMENTING THEREOF", the entire contents of which are incorporated in this application by reference.

BACKGROUND OF THE DISCLOSURE

Around seventy percent of medical professionals will misuse prescription drugs at least once during their career. This shocking statistic may be attributed to the long or inconsistent working hours, the increased exposure to trauma, the stress of the job, or some mental or physical pain. For many of these professionals, including EMTs, physicians, nurses, and technicians, this misuse may be a one-time occurrence. However, around 10-15% of medical professionals that misuse prescription drugs do so repeatedly to the extent of drug dependency or addiction.

One reason that so many medical professionals abuse drugs is the ready availability of the drugs. In many situations, only a fraction of drugs is used on patients and the unused portion is intended to be discarded. Instead of discarding the drugs, however, the remaining drugs may be lost, misplaced, or stolen allowing the healthcare professionals to access the drugs and abuse them with no way of tracking their use and abuse. The failure of the healthcare system to track drugs at every stage contributes to the growing issue of medical professional misuse of prescription substances.

Currently, there is no waste management system in place to track the remaining drugs after some are used. Eventually, wasted drugs are discarded and destroyed. Hazardous waste boxes are common disposal techniques in healthcare settings. Unfortunately, these boxes are not secure enough to prevent healthcare professionals or others with access to the boxes from obtaining the used drugs from the waste boxes once they are placed in there. This system also does not stop someone from pocketing the drugs instead of properly discarding them.

SUMMARY OF THE DISCLOSURE

What is needed is a system that allows for the tracking of narcotics waste. Accordingly, the present disclosure relates to systems that rely on a self-locking cover to limit access to narcotics. In some embodiments, a self-locking cover may allow for a single access opportunity to a narcotics vial, which may be one or both original vials and waste vials. In some aspects, a self-locking cover may be incorporated into narcotics transportation and tracking mechanisms, which may allow for increased security against tampering or abuse of narcotics, particularly narcotics waste. Self-locking covers may prevent uninhibited and free access to waste narcotics, which may be susceptible to abuse.

In some embodiments, a smart narcotics case may incorporate waste vials with self-locking covers. In some implementations, the smart narcotics case may comprise a series of recesses, wherein access to the recesses is controlled by self-locking covers. In some aspects, the narcotics within the recesses and waste vials may be removable or emptied by persons with accessibility permission. In some embodiments, the smart narcotics case may incorporate or accept original vials with self-locking covers. In some implementations, a smart narcotics case may comprise one or more sensors and detectors that may track and measure narcotics usage between original and waste vials. In some aspects, one or more a smart narcotics case and waste vials may interact with external monitoring and tracking systems that may further track transportation and use of narcotics.

The present disclosure relates to a system with self-locking cover for drug waste management comprising a plurality of vials configured to contain narcotics, where each of the plurality of vials may comprise a container portion configured to contain narcotics; a self-locking cover configured to allow for single access to the narcotics; a smart narcotics case configured to store the plurality of vials, where the smart narcotics case may comprise a base comprising a plurality of recesses, where each of the plurality of recesses may be configured to accept each of the plurality of vials, and a lid that may comprise a plurality of openings, where each of the plurality of openings may be located proximate to each of the self-locking covers of each of the plurality of vials.

In some embodiments, the self-locking cover may comprise a plurality of tabs extending laterally, and where the plurality of openings further accept the plurality of tabs. In some implementations, the self-locking cover may comprise a syringe canal extending perpendicularly downward into the container portion. In some aspects, the syringe canal may comprise aeration openings. In some embodiments, the self-locking cover may comprise a spring mechanism extending laterally from an interior side of the self-locking cover; a syringe opening configured to accept a syringe; and a flexible panel configured to receive the syringe for single access, where once the syringe may be removed from the self-locking cover, the spring mechanism engages the flexible panel to block the syringe opening.

In some aspects, the lid may be lockable to the base. In some embodiments, one or both the base and the lid may comprise one or more narcotics indicator. In some implementations, at least a portion of the plurality of recesses may comprise a sensor in logical communication with the one or more narcotics indicator, where data from the sensor may be transmittable to the one or more narcotics indicator. In some aspects, the sensor may be configured to measure volume, and at least a portion of the one or more narcotics indicator indicates volume of the narcotics remaining in at least one of the plurality of vials. In some embodiments, the sensor may be configured to detect narcotics type, and at least a portion of the one or more narcotics indicator indicates narcotics type contained in at least one of the plurality of vials.

In some implementations, the present disclosure relates to a vial with self-locking cover. In some aspects, the vial may include a container portion configured to contain narcotics; and a self-locking cover configured to allow for single access to the narcotics, where the self-locking cover may comprise a syringe opening configured to accept a syringe into the container portion.

In some embodiments, the self-locking cover may comprise a spring mechanism extending laterally from an interior side of the self-locking cover; a flexible panel configured to receive the syringe for single access, where once the syringe may be removed from the self-locking cover, the spring mechanism engages the flexible panel to block the syringe opening.

In some implementations, the present disclosure relates to a method for tracking narcotics waste. In some aspects, the method includes receiving a first vial of narcotics into a smart narcotics case; detecting a first amount of narcotics in the first vial; providing single access to narcotics in the first vial; detecting a waste amount of narcotics remaining in the first vial; transmitting data about the waste amount of narcotics, where the data may comprise at least the waste amount of narcotics; and releasing the first vial of narcotics.

In some embodiments, the narcotics may comprise a liquid and access to the narcotics may be limited to a syringe. In some implementations, the narcotics may comprise a capsule, tablet, or solid form. In some aspects, tracking determines at least a current location of the vial. In some embodiments, the smart narcotics case may comprise a wireless mechanism, and where transmission of data occurs wirelessly. In some implementations, the data may comprise the narcotics type. In some aspects, the first vial may comprise a container portion configured to contain narcotics, and a self-locking cover configured to allow for single access to the narcotics.

In some embodiments, the smart narcotics case may comprise: a base may comprise at least one recess, where the at least one recess may be configured to accept the first vial, and a lid may comprise at least one opening, where the at least one opening may be located proximate to the self-locking cover, allowing single access to the narcotics.

BRIEF DESCRIPTION OF THE DRAWINGS

The accompanying drawings that are incorporated in and constitute a part of this specification illustrate several embodiments of the disclosure and, together with the description, serve to explain the principles of the disclosure:

FIG. 5A illustrates a cross-section view of an empty waste vial with an exemplary self-locking cover and narcotics indicator, according to some embodiments of the present disclosure.

FIG. 5B illustrates a cross-section view of a series of narcotics levels for a waste vial with an exemplary self-locking cover and narcotics indicator, according to some embodiments of the present disclosure.

FIG. 11A illustrates a perspective view of an exemplary self-locking cover with stopper, according to some embodiments of the present disclosure.

FIG. 11B illustrates a side view of an exemplary self-locking cover with stopper, according to some embodiments of the present disclosure.

FIG. 13A illustrates a perspective view of an exemplary self-locking cover, according to some embodiments of the present disclosure.

FIG. 13B illustrates a side view of an exemplary self-locking cover, according to some embodiments of the present disclosure.

FIG. 13C illustrates a top-down view of an exemplary self-locking cover, according to some embodiments of the present disclosure.

FIG. 14 illustrates a side view of an exemplary self-locking cover with a spring mechanism, according to some embodiments of the present disclosure.

DETAILED DESCRIPTION

Figure 1:
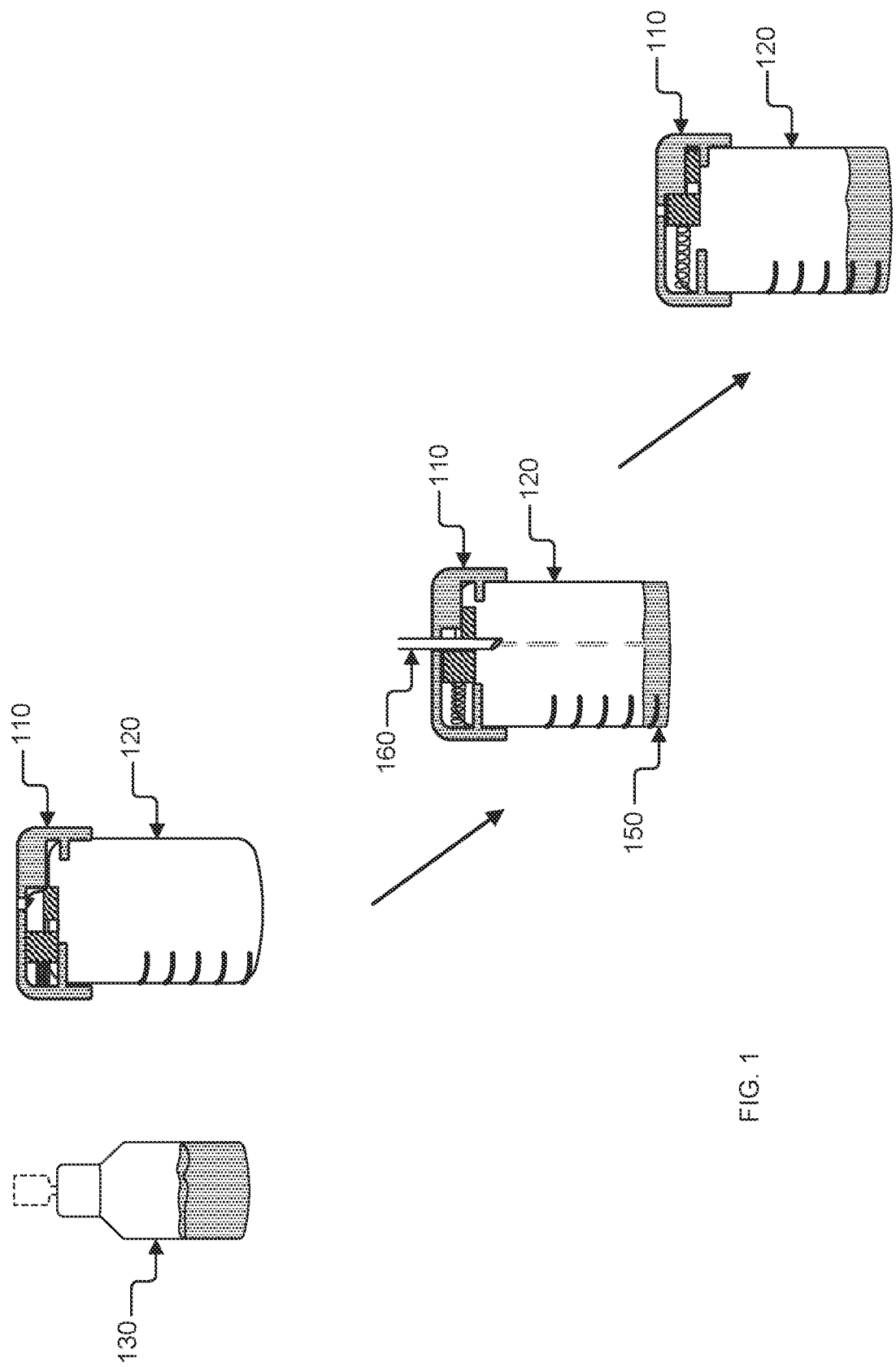
FIG. 1 illustrates exemplary transfer of narcotics from an original vial to a waste vial a self-locking cover, according to some embodiments of the present disclosure.

The present disclosure relates to systems that rely on a self-locking cover to limit access to narcotics. In some embodiments, a self-locking cover may allow for a single access opportunity to a narcotics vial, which may be one or both original vials and waste vials. In some aspects, a self-locking cover may be incorporated into narcotics transportation and tracking mechanisms, which may allow for increased security against tampering or abuse of narcotics, particularly narcotics waste. Self-locking covers may prevent uninhibited and free access to waste narcotics, which may be susceptible to abuse.

In the following sections, detailed descriptions of examples and methods of the disclosure will be given. The description of both preferred and alternative examples, though thorough, are exemplary only, and it is understood to those skilled in the art that variations, modifications, and alterations may be apparent. It is therefore to be understood that the examples do not limit the broadness of the aspects of the underlying disclosure as defined by the claims.

Embodiments that may comprise communication between devices may rely on standard communication mechanisms, including wireless systems, such as RFID, NFC, Bluetooth, or infrared technologies, and wired systems. Even where specifically identified, it is understood to those skilled in the art that a range of communication mechanisms may be practical and useful. Similarly, references to sensing or indicating mechanisms may be depicted as a specific embodiment, but other variations may be understood to those skilled in the art.

Glossary
- Self-locking cover: as used herein refers to a locking mechanism that may allow for a single access opportunity. A self-locking cover may be insertable into an access or insertion panel, wherein the self-locking cover may be separate from a vial. A self-locking may comprise a lid that may be attached, adhered, or tightened onto a vial. In some aspects, a self-locking mechanism may be for one-time use and then discarded. Where attached to a vial, the self-locking mechanism may be transported with the vial. In some embodiments, a self-locking cover may be resettable.
- Original vial: as used herein refers to a container of unused narcotics. An original vial may comprise loose narcotics, such as pills, capsules, powders, or liquid. An original vial may be provided from narcotics suppliers. In some embodiments, an original vial may contain a sub-container.
- Waste vial: as used herein refers to a container of narcotics waste that may be leftover from an original vial after a dose has been administered. In some aspects, a waste vial may comprise a portable and independent container. In some embodiments, a waste vial may comprise a portion of a smart narcotics case, such as recess or insert. Where the term vial is used, either original vial or waste vial may be applicable without a feature specific to either type.
- Smart narcotics case: as used herein refers to a portable system for carrying vials, wherein at least a portion of the vials comprise a self-locking cover. A smart narcotics case may comprise narcotics indicators, which may provide information related to transfer of narcotics between original vial and waste vial.

Referring now to FIG. 1, an exemplary transfer of narcotics 150 from an original vial 130 to a waste vial 120 with a self-locking cover 110 is illustrated. In some embodiments, an original vial 130 may comprise an outer capsule that may contain a separate narcotics container, such as one shipped from a manufacturer or supplier. In some aspects, an original vial 130 and waste vial 120 may be transported together, wherein once narcotics 150 are used, the waste may be transferred to a waste vial 120 with a self-locking cover 110.

In some implementations, a self-locking cover 110 may allow for a single insertion of a syringe 160, which may trigger the self-locking cover 110. This may reduce the risk of tampering or access to the waste.

Figure 2A:
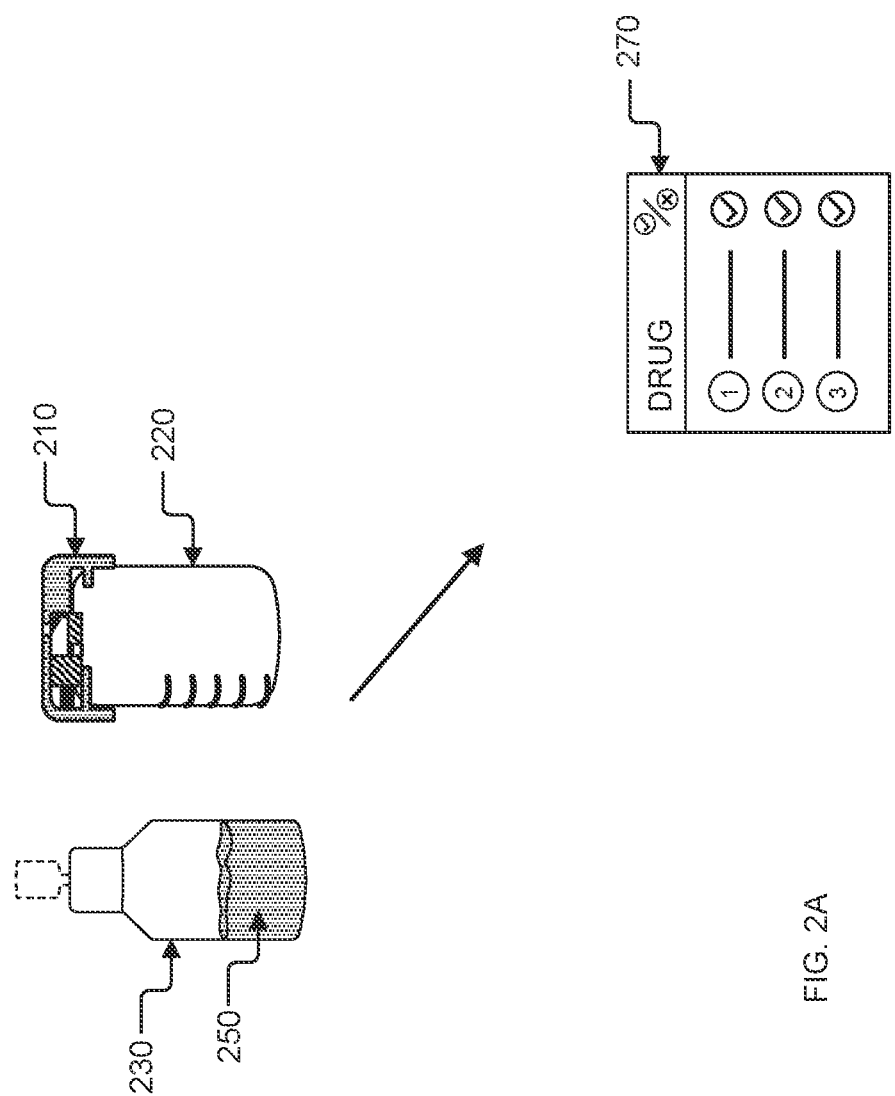
FIG. 2A illustrates exemplary steps for tracking use of narcotics, wherein the original vial is unopen, according to some embodiments of the present disclosure.

Referring now to FIG. 2A, exemplary steps for tracking use of narcotics 250 are illustrated, wherein the original vial 230 is unopen. In some aspects, one or both an original vial 230 and waste vial 220 with self-locking cover 210 may be trackable, wherein narcotics 250 use and waste may be tracked. In some embodiments, a tracking system may output narcotics information 270. For example, where all original vials 230 are unopen and none of the narcotics 250 have been accessed, the narcotics information 270 may reflect that.

Figure 2B:
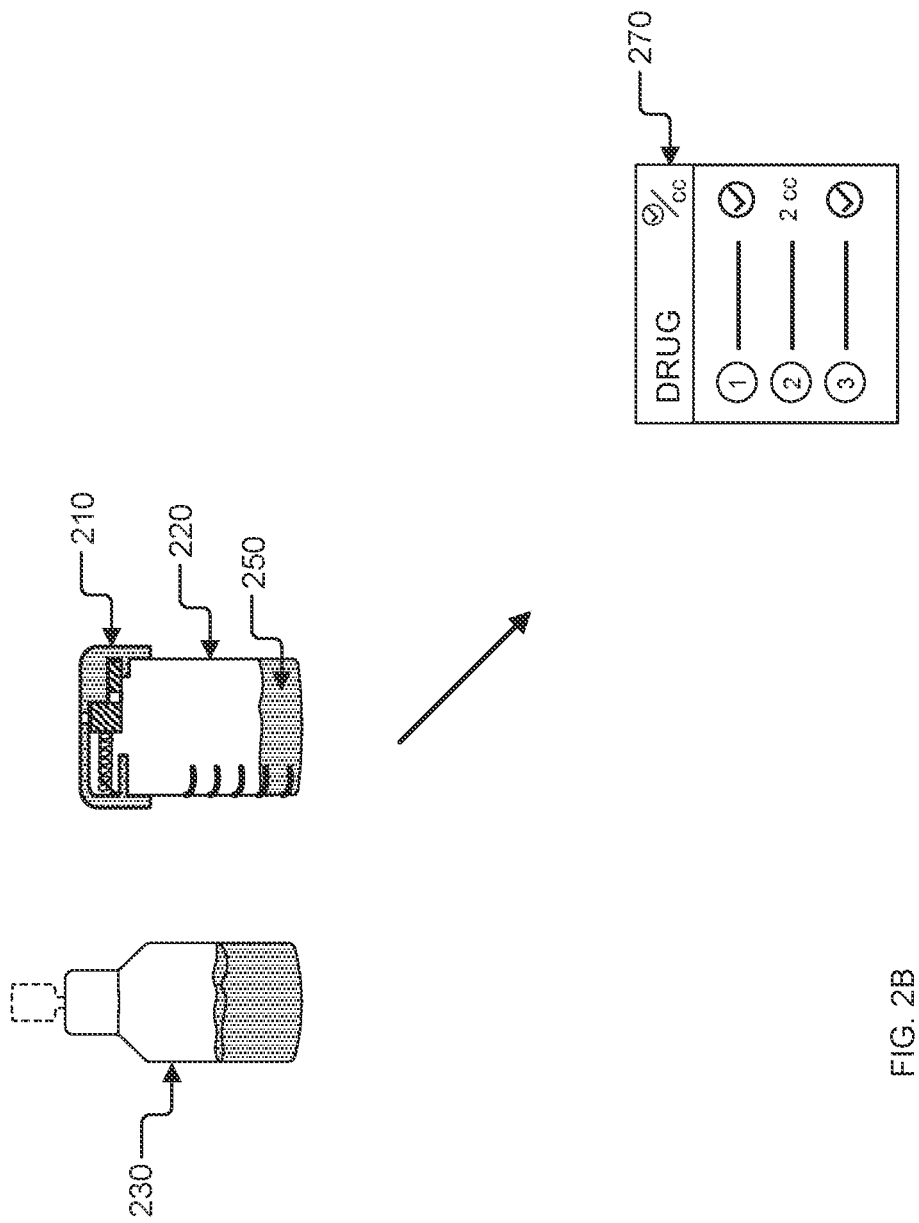
FIG. 2B illustrates exemplary steps for tracking use of narcotics, wherein at least a portion of the narcotics have been used, according to some embodiments of the present disclosure.

Referring now to FIG. 2B, exemplary steps for tracking use of narcotics 250 are illustrated, wherein at least a portion of the narcotics 250 have been used. In some embodiments, a tracking system may detect when an original vial 230 may be opened. In some aspects, a tracking system may detect when narcotics 250 are added to a waste vial 220. In some implementations, triggering the self-locking cover 210 may be detectable. In some aspects, a tracking system may be able to detect an amount of waste in the waste vial 220, wherein output narcotics information 270 may indicate whether an original vial 230 has been accessed and how much narcotics 250 is in the waste vial 220.

Figure 3A:
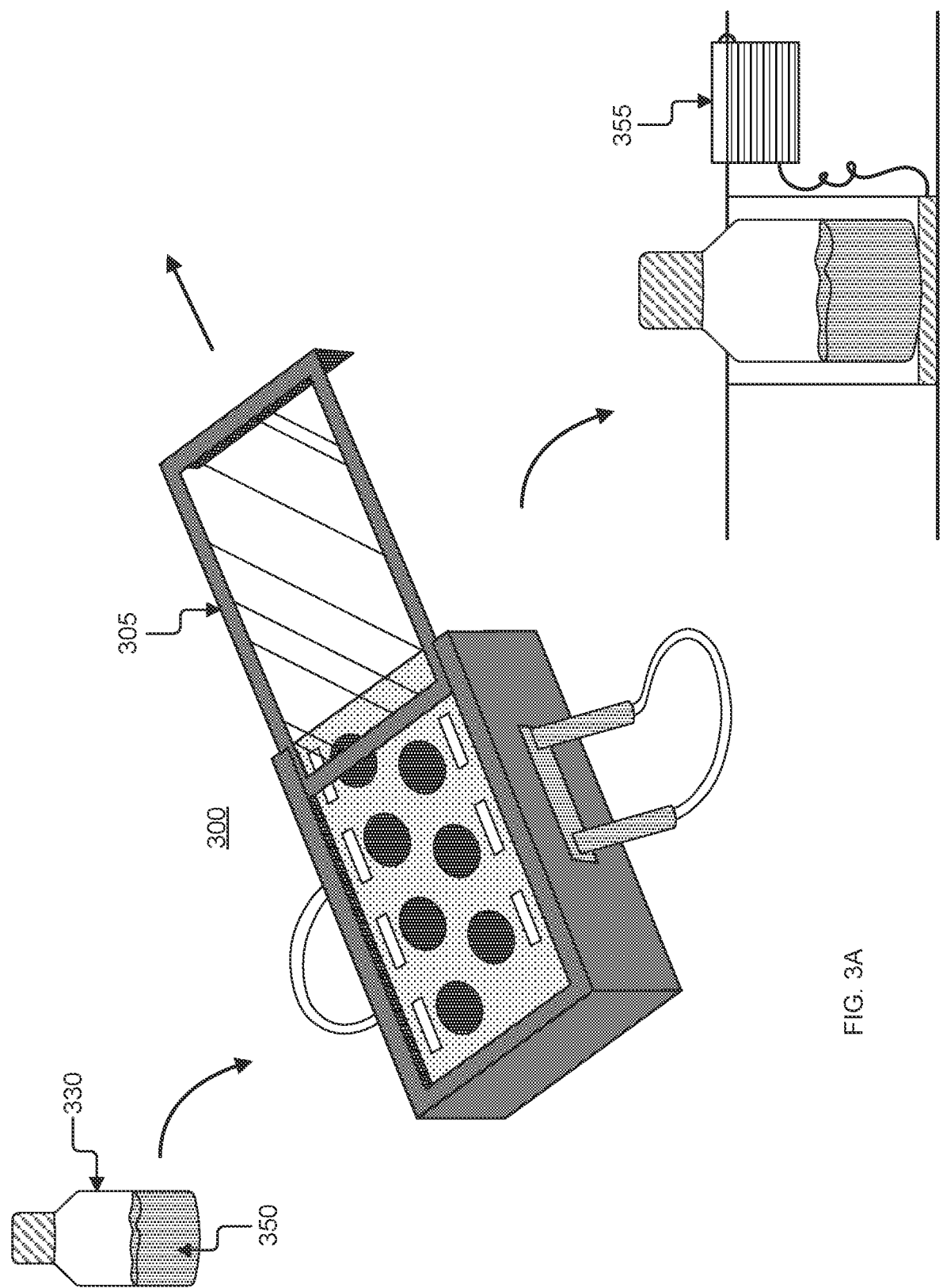
FIG. 3A illustrates an exemplary embodiment of inserting an unopen original vial into a smart narcotics case with a narcotics indicator for an original vial, according to some embodiments of the present disclosure.

Referring now to FIG. 3A, an exemplary embodiment of inserting an unopen original vial 330 into a smart narcotics case 300 with a narcotics indicator 355 for an original vial 330 is illustrated. In some aspects, a smart narcotics case 300 may comprise recesses to accept original vials 330 and waste vials, wherein at least a portion of the recesses comprise a narcotics indicator 355. In some embodiments, the narcotics indicator 355 may comprise a sensor or scale that may detect amounts of narcotics 350 within the original vial 330. For example, the original vial 330 may comprise a known weight. The narcotics indicator 355 may detect whether the original vial 330 has been open, wherein an initial full weight may be detected and stored. A change in the weight may trigger a notification that the narcotics 350 have been used or removed.

In some aspects, a smart narcotics case 300 may comprise a lid 305. In some embodiments, the lid 305 may be slid into place over the vials 330, 320, wherein any access to the vials 330, 320 may be tracked. For example, the lid 305 may comprise a magnetic rim that engages with the smart narcotics case 300, and disengagement of the magnetic connection may trigger a notification, such as to a supervisor or tracking system.

Figure 3B:
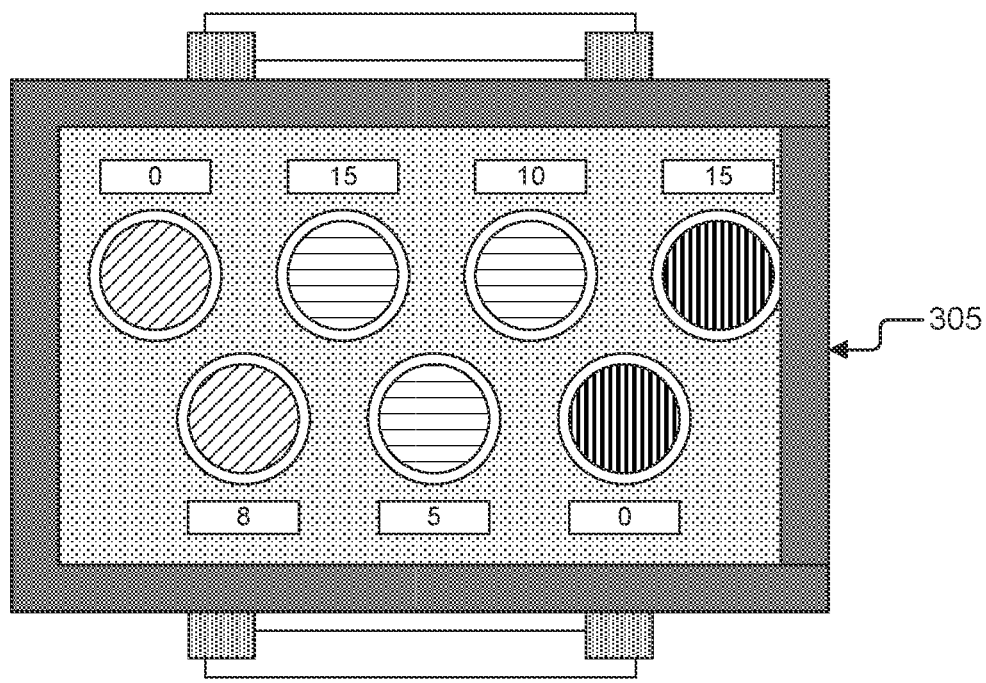
FIG. 3B illustrates an exemplary embodiment of matching patterns between original vials and waste vials for the same narcotics, according to some embodiments of the present disclosure.

Referring now to FIG. 3B, an exemplary embodiment of matching patterns between original vials and waste vials for the same narcotics. In some aspects, for ease of reference, original vials and waste vials for the same narcotics may comprise matching patterns. In some embodiments, the smart narcotics case 300 may comprise a clear lid 305, which may allow for visibility of the coordinated patterns. Coordinated patterns may allow for multiple narcotics types to be separately and securely stored. A person inserting waste into a waste vial can match to the correct waste vial, and a person who has access and permissions to remove the waste vials will know which waste vials contain which narcotics.

Figure 3C:
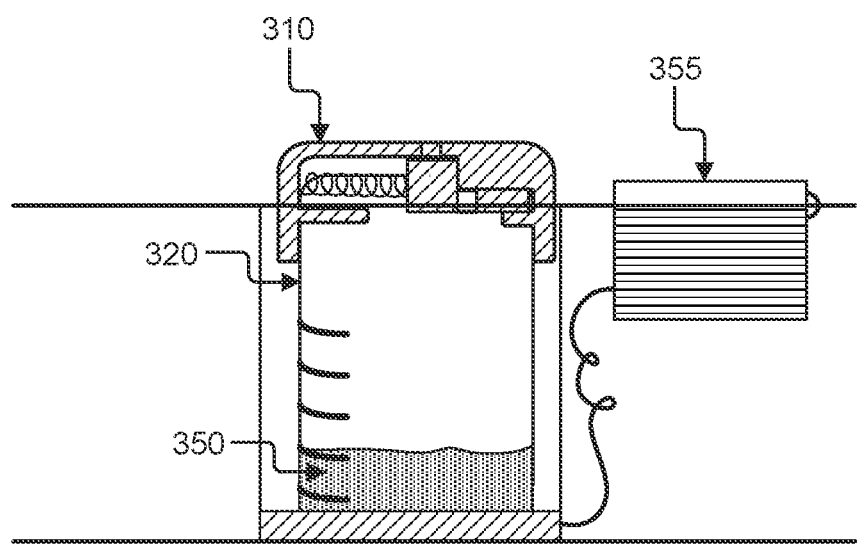
FIG. 3C illustrates an exemplary embodiment of a narcotics indicator for a waste vial, according to some embodiments of the present disclosure.

Referring now to FIG. 3C, an exemplary embodiment of a narcotics indicator 355 for a waste vial 320 with self-locking cover 310 is illustrated. In some aspects, a smart narcotics case may comprise recesses with narcotics indicators 355 for waste, wherein presence or weight of the waste vial 320 may be detected. In some embodiments, a waste vial 320 may comprise a known base weight, and a narcotics indicator 355 may detect a change in weight. In some implementations, the narcotics indicator 355 may provide narcotics details, such as narcotics levels for any vial 320, 330 within a smart narcotics case 300.

Figure 4:
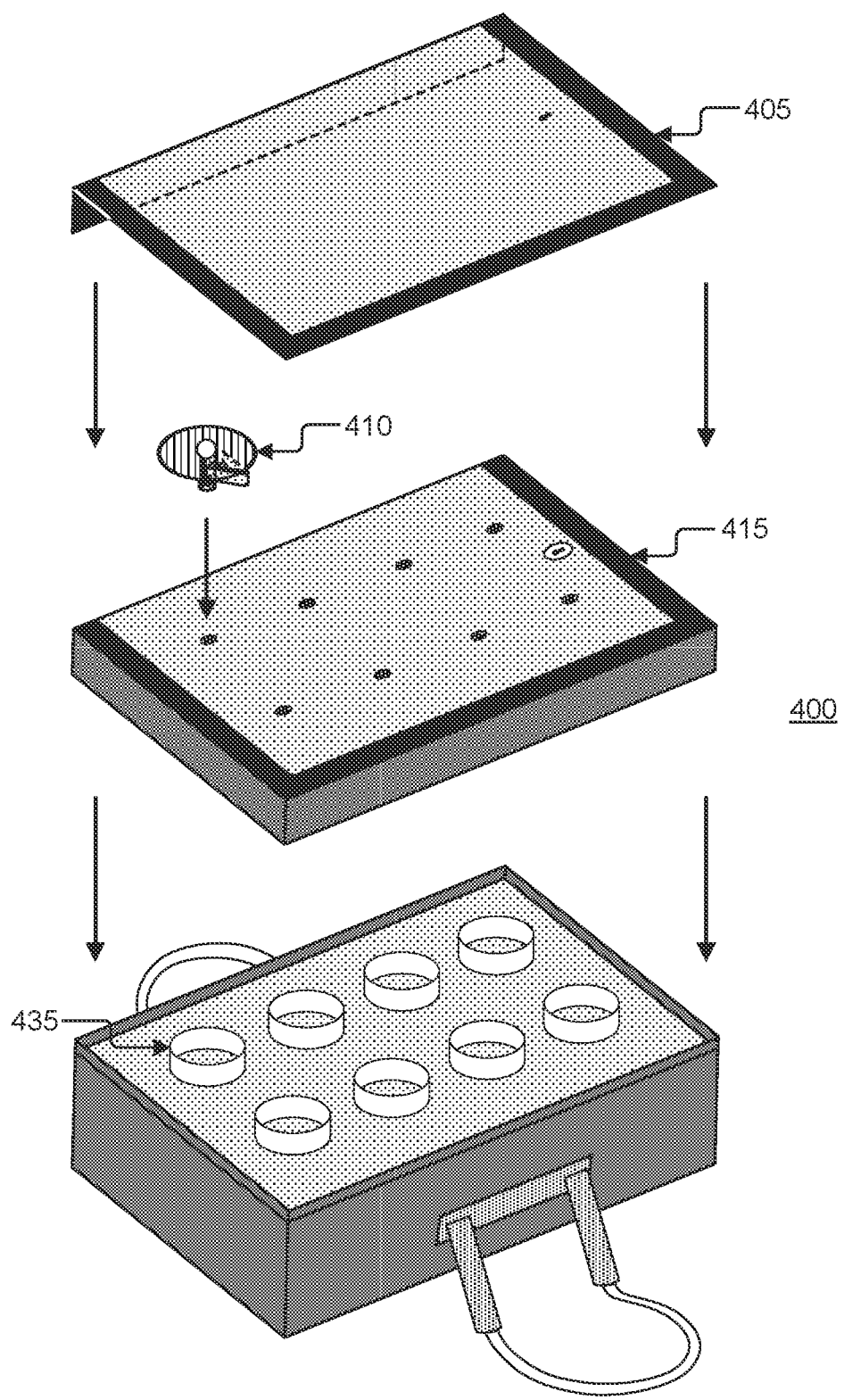
FIG. 4 illustrates a partially exploded view of an exemplary smart narcotics case configured to accept self-locking covers, according to some embodiments of the present disclosure.

Referring now to FIG. 4, a partially exploded view of an exemplary smart narcotics case 400 configured to accept self-locking covers 410 is illustrated. In some aspects, a smart narcotics case 400 may comprise a series of recesses 435 that may accept narcotics. In some embodiments, separate vials may be insertable into the recesses 435, such as waste vials and original vials. In some embodiments, a smart narcotics case 400 may be dedicated to only waste vials or only original vials, which may allow for a universal vial type within the smart narcotics case 400. The smart narcotics case 400 may allow for a mix of original vials and waste vials, which may allow for convenient portability of both vial types within the same smart narcotics case 400.

In some implementations, a smart narcotics case 400 may comprise an insertion layer 415, which may accept syringes and allow access to the recesses 435. In some aspects, the insertion layer 415 may accept self-locking covers 410, which may be individually inserted and configured. In some embodiments, a lid 405 may attach and cover the insertion layer 415. In some embodiments, an insertion layer 415 may comprise a series of self-locking covers 410. In some aspects, the self-locking covers 410 may be replaceable, wherein once locked narcotics are removed, another self-locking cover 410 may replace it.

In some embodiments, self-locking covers 410 may be resettable, wherein the self-locking cover 410 may be disengaged again, allowing for another access opportunity. The resetting may be manual or automatic, such as through an electronic command. Access to the addition, removable, or resetting or self-locking covers 410 may be limited to specific individuals, such as supervisors or narcotics specialists.

In some implementations, the lid 405 and insertion layer 415 may comprise locks that may limit access to one or more the recesses, insertion layer 415, and self-locking covers 410. In some embodiments, the lock may be mechanical, such as requiring a physical key. In some aspects, the lock may be electronic, such as requiring a digital code or other access key. In some implementations, the lock may comprise a combination of mechanical and electronic locks, which may provide multiple layers of protection limiting risk of tampering and unapproved access to the narcotics.

Referring now to FIG. 5A, a cross-section view of an empty waste vial 520 with an exemplary self-locking cover 510 and narcotics indicator 555 is illustrated. In some embodiments, a waste vial 520 may be connected to or placed proximate to a narcotics indicator 555, which may allow for tracking of narcotics. In some aspects, a self-locking cover 510 may comprise a stopper that keeps the self-locking cover 510 open, wherein insertion of a syringe may push the stopper out, allowing for initial access to the waste vial 520. Once the syringe is removed, the self-locking cover 520 may be in a locked position, which may prevent further access to the narcotics.

Referring now to FIG. 5B, a cross-section view of a series of narcotics levels for a waste vial 520 with an exemplary self-locking cover 510 and narcotics indicator 555 is illustrated. In some aspects, narcotics levels for a waste vial 520 may be tracked, wherein loss of narcotics 550 may trigger transmission of a notification, such as to a supervisor or system. In some embodiments, disengagement of the self-locking cover 510 may prompt an initial narcotics level reading by a narcotics indicator 555. In some implementations, detection of a loss in narcotics may indicate tampering, triggering a notification.

Though shown as tracking narcotics in a waste vial 520, a similar mechanism may track narcotics use from an original vial. In some embodiments, an original vial may comprise a self-locking cover, and an insertion of a syringe may disengage the self-locking cover. The initial use may prompt detection of a narcotics level, wherein any change in narcotics level may suggest or indicate tampering.

Figure 6A:
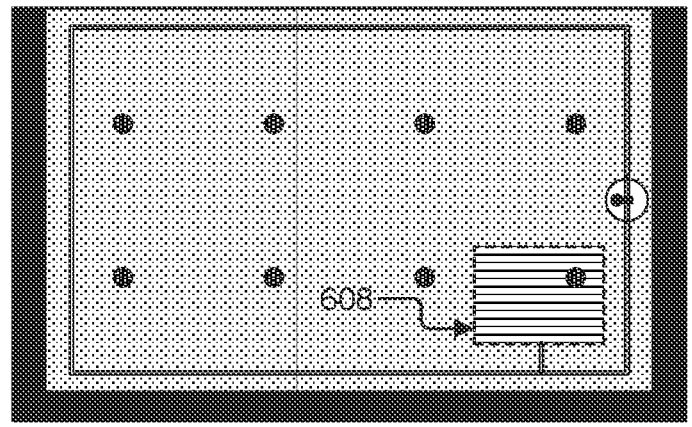
FIG. 6A illustrates an exemplary smart narcotics case with an access sensor, according to some embodiments of the present disclosure.
Figure 6B:
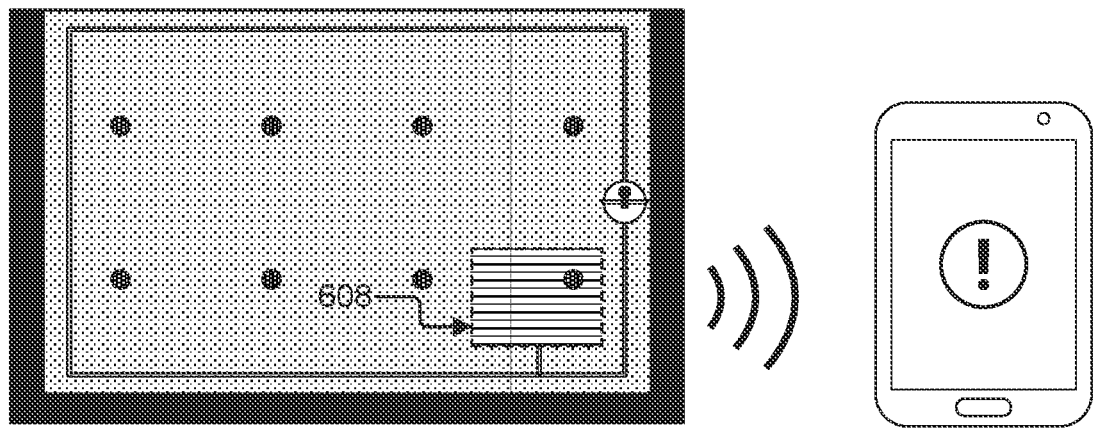
FIG. 6B illustrates an exemplary smart narcotics case with an access sensor, wherein access has been detected, according to some embodiments of the present disclosure.

Referring now to FIG. 6A, an exemplary smart narcotics case 600 with an access sensor 608 is illustrated. Referring now to FIG. 6B, an exemplary smart narcotics case 600 with an access sensor 608 illustrated, wherein access has been detected. In some embodiments, a smart narcotics case 600 may comprise multiple layers of access protection, which may further limit the risk of tampering or abuse of the narcotics. In some implementations, an access sensor 608 may track access to the vials. In some aspects, any access may trigger a notification. In some embodiments, one or both notifications and tracking may be based on access types.

For example, removing a sliding lid to access vials or insertion layer may indicate use, which may be standard or typical for daily use by a health care professional. Removing the vial cover or insertion layer may indicate direct and open access to the narcotics. Removal of the sliding lid may be tracked, and removing the vial cover or insertion layer may trigger a notification. A notification may be transmitted to one or more recipients, such as an organizational system, supervisor, or narcotics department. In some embodiments, a user may have the ability to override or acknowledge that the access was permissible.

Figure 7:
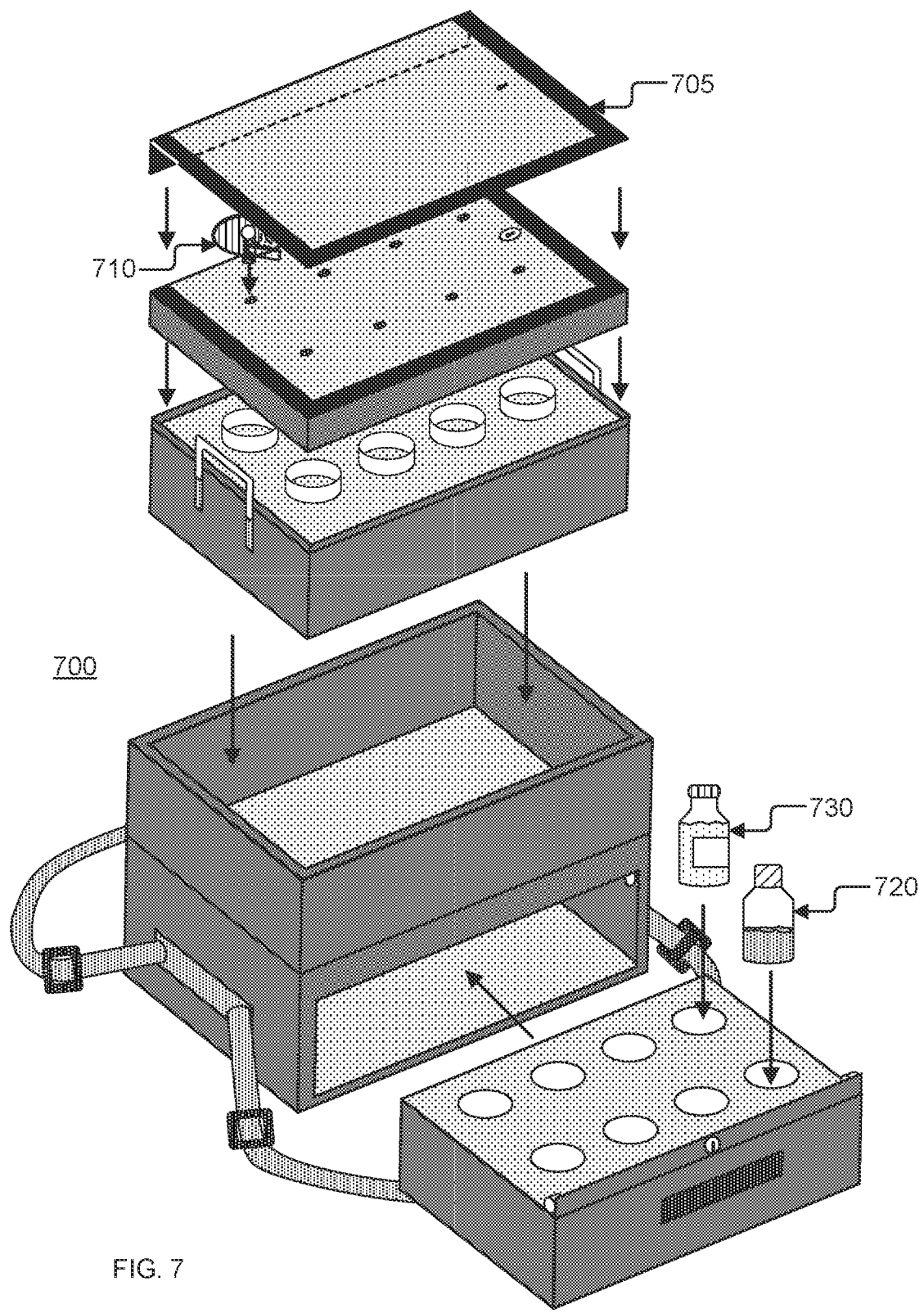
FIG. 7 illustrates a partially exploded view of a smart narcotics case for original vials and waste vials, according to some embodiments of the present disclosure.

Referring now to FIG. 7, a partially exploded view of a smart narcotics case 700 with lid 705 for original vials 730 and waste vials 720. In some embodiments, a smart narcotics case 700 may comprise multiple compartments, which may allow for separation of waste vials 720 and original vials 730. In some aspects, a bottom drawer may accept and store original vials 730. The original vials 730 may comprise a self-locking cover, a trackable cover, or standard cover. In some aspects, the cover type for original vials 730 may depend on regulations associated with each narcotics types. For example, aspirin may require a standard tamper-proof lid, and opioids may require multiple levels off access protections.

In some aspects, a separate top compartment may be designated for waste vials 720, wherein access to the waste vials 720 may be protected by self-locking covers 710. Similar to the original vials, self-locking covers 710 may be required for specific types of narcotics, such as those typically associated with abuse. For example, a liquid antiemetic may not require a self-locking cover 710, but waste may be tracked or require specific disposal protocols.

Figure 8A:
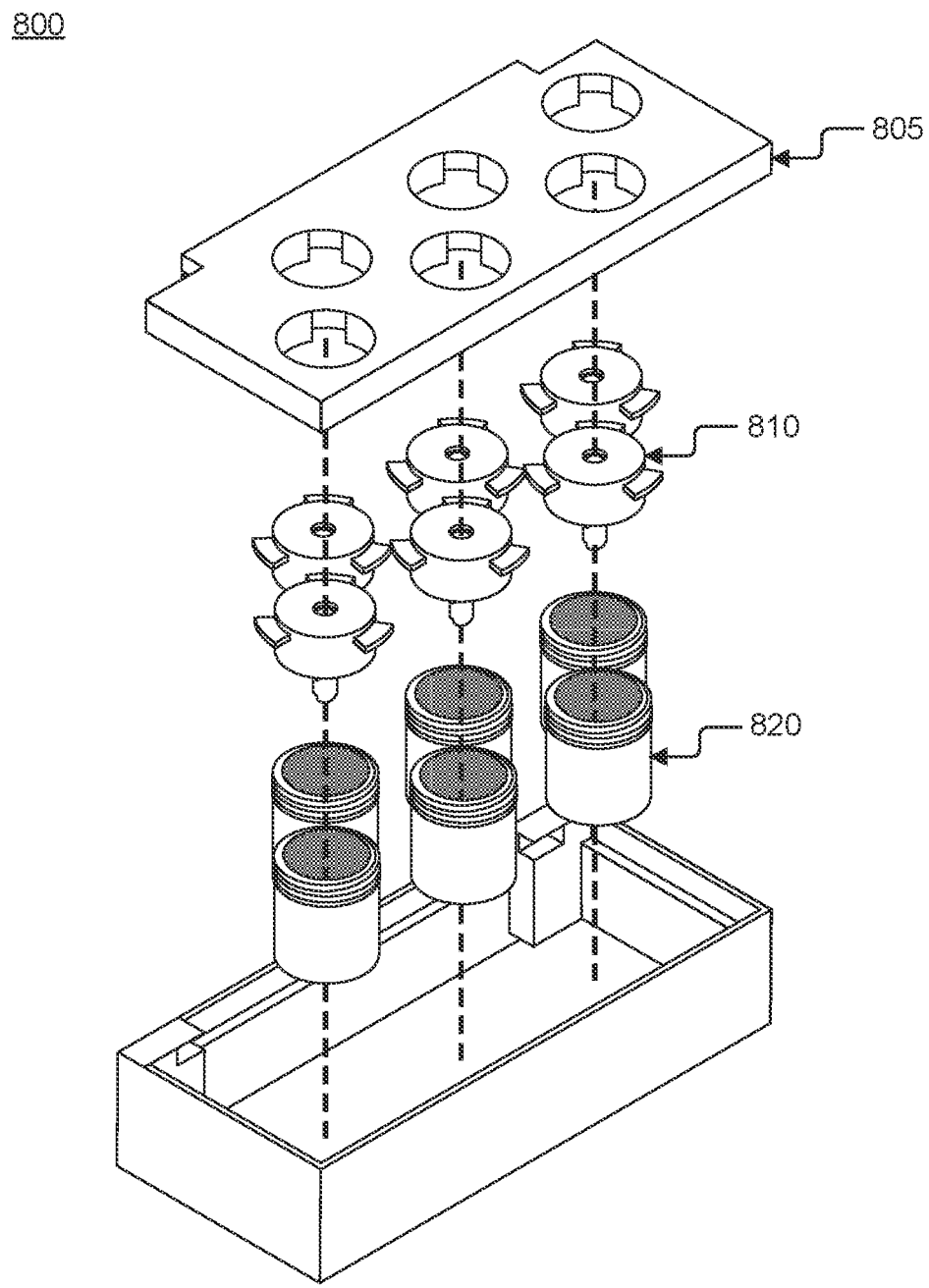
FIG. 8A illustrates an exploded view of an exemplary smart narcotics case with vials, according to some embodiments of the present disclosure.
Figure 8B:
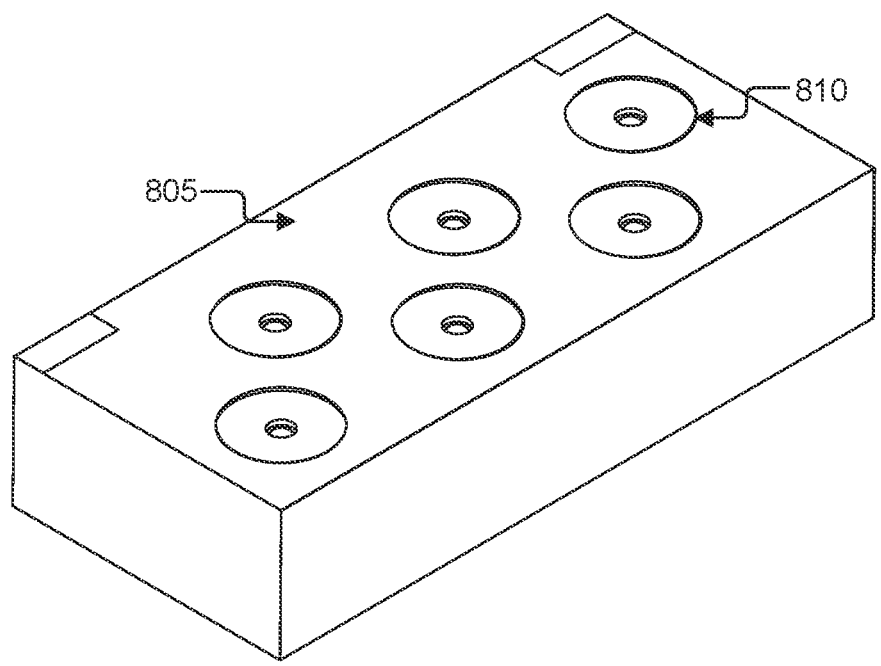
FIG. 8B illustrates a closed view of an exemplary smart narcotics case with vials, according to some embodiments of the present disclosure.

Referring now to FIG. 8A, an exploded view of an exemplary smart narcotics case 800 with vials 810, 820 is illustrated. Referring now to FIG. 8B, a closed view of an exemplary smart narcotics case 800 with vials 810, 820 is illustrated. In some aspects, a vial may comprise a containing portion 820 and a self-locking cover 810. In some embodiments, a smart narcotics case 800 may comprise a lid 805 that may accept self-locking cover 810, wherein self-locking cover 810 may be locked into the lid 805 of the smart narcotics case 800.

Figure 8C:
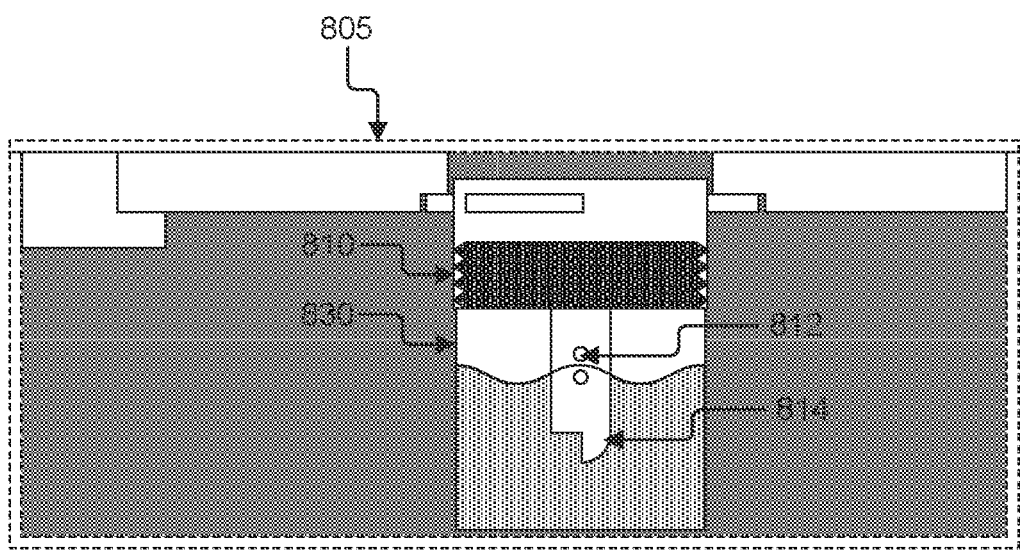
FIG. 8C illustrates a cross section side view of an exemplary smart narcotics case with a vial, according to some embodiments of the present disclosure.
Figure 8D:
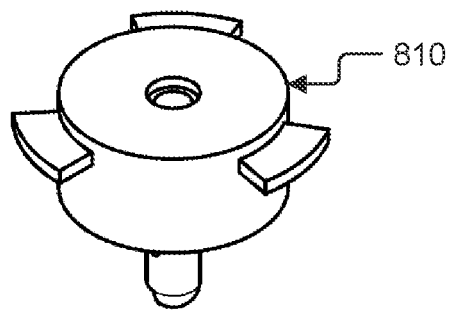
FIG. 8D illustrates a top-down view of an exemplary vial lid, according to some embodiments of the present disclosure.
Figure 8E:
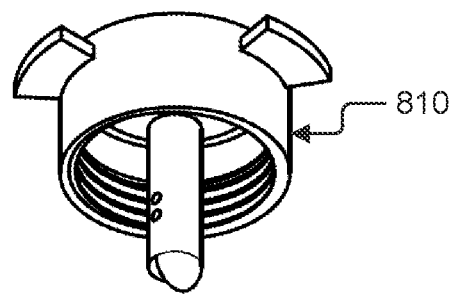
FIG. 8E illustrates a bottom-up view of an exemplary vial lid, according to some embodiments of the present disclosure.

Referring now to FIG. 8C, a cross section side view of an exemplary smart narcotics case 800 with a vial 810, 820 is illustrated. Referring now to FIGS. 8D-8E, an exemplary self-locking cover 810 is illustrated. In some aspects, a self-locking cover 810 may comprise tabs extending laterally, which may allow for a locking interface with a smart narcotics case 800. In some embodiments, the self-locking cover 810 may comprise a syringe canal 814 configured to accept a syringe, which may allow for syringe access to the narcotics contained in the vial. In some implementations, the syringe canal 814 may comprise aeration openings 812 to allow for free flow of the liquid narcotics.

Figure 9A:
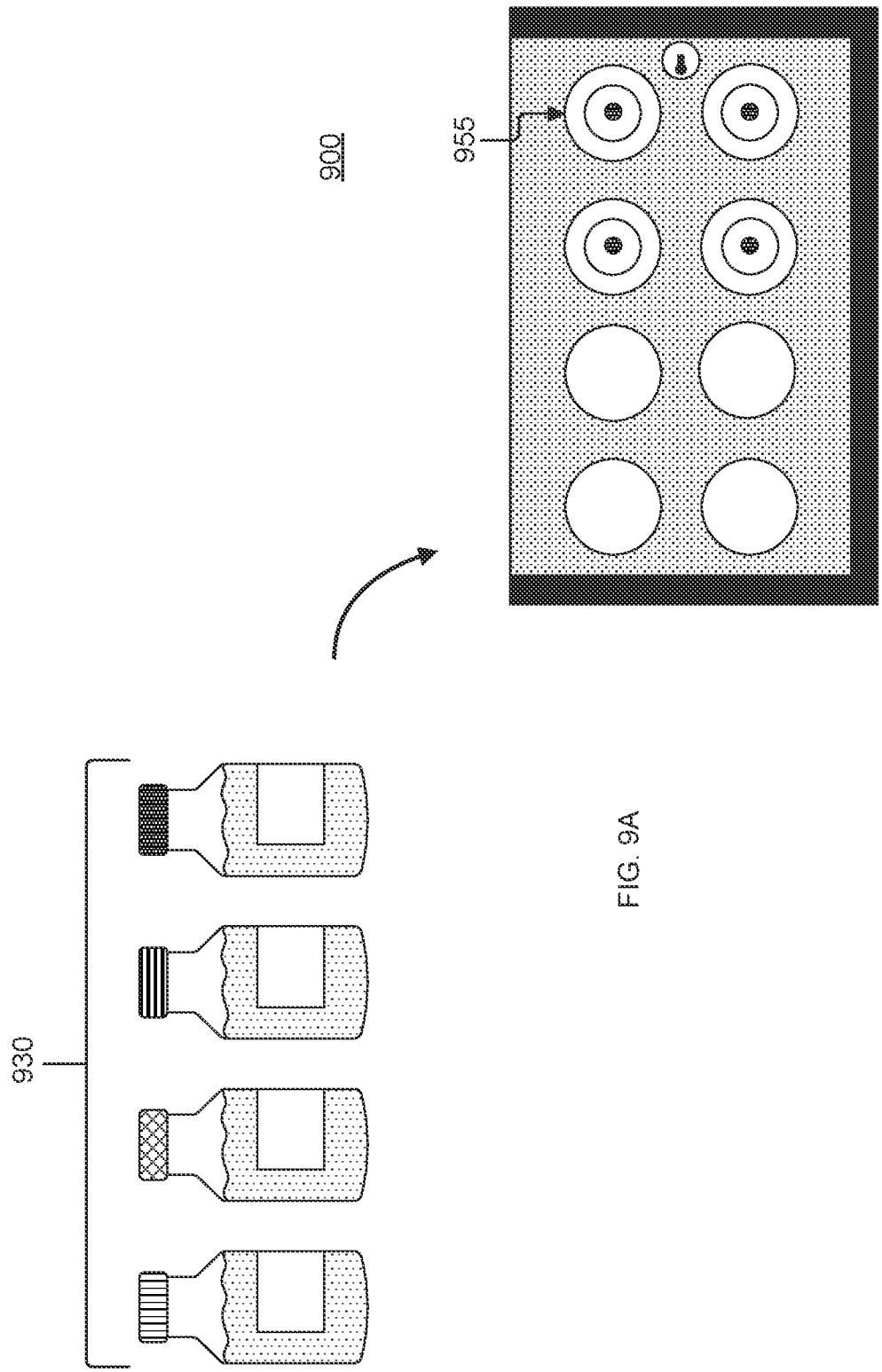
FIG. 9A illustrates original vials and an empty exemplary smart narcotics case with narcotics indicators, according to some embodiments of the present disclosure.

Referring now to FIG. 9A, original vials 930 and an empty exemplary smart narcotics case 900 with narcotics indicators 955 are illustrated. In some aspects, a smart narcotics case 900 may comprise a series of recesses that are configured to receive original vials 930. In some embodiments, a smart narcotics case 900 may comprise narcotics indicators 955, which may indicate the type of narcotics contained in one or more original vial 930 or waste vial. In some implementations, the narcotics indicators 955 may be active, which may allow for dynamic labeling and coordination.

Figure 9B:
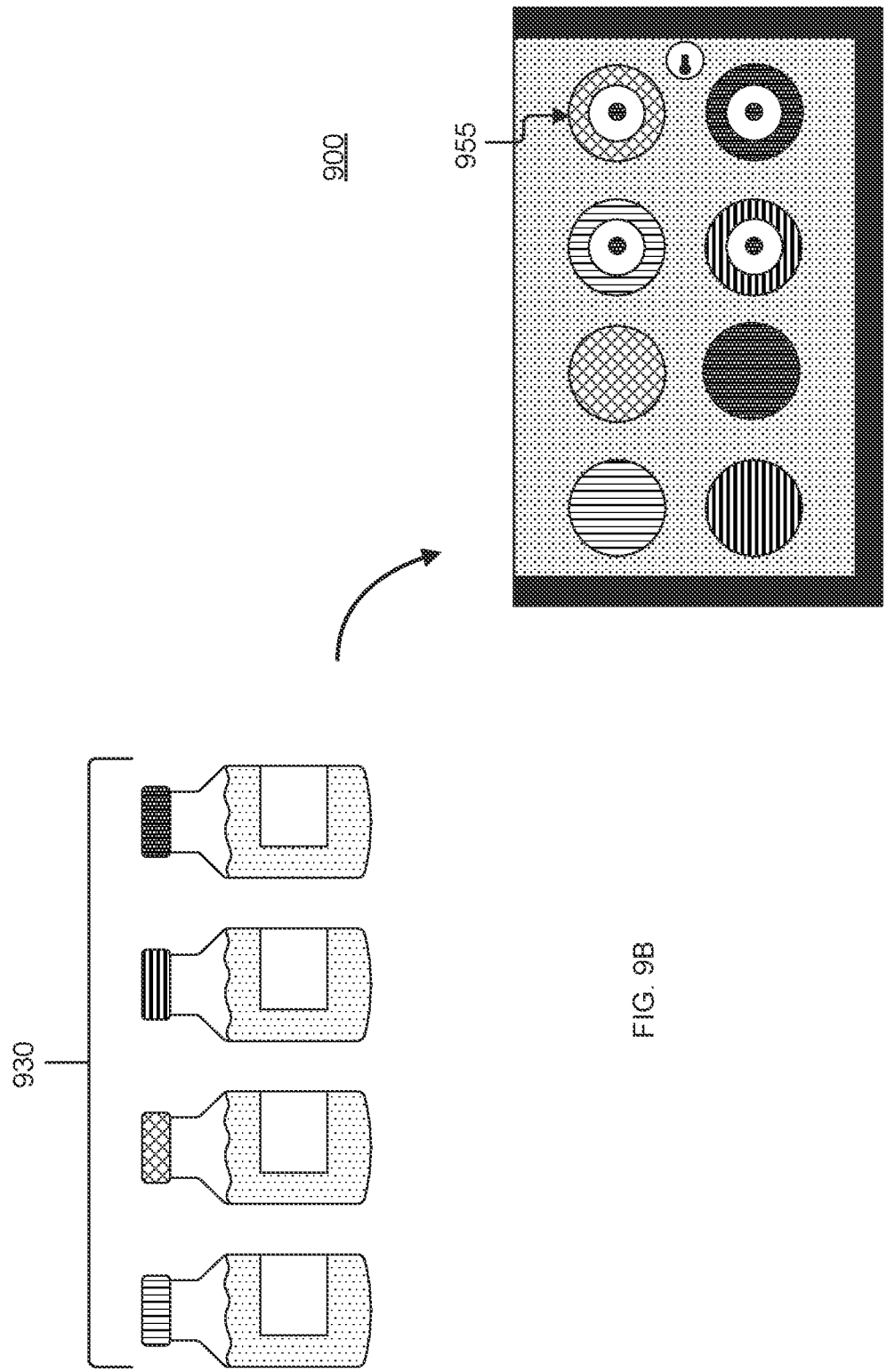
FIG. 9B illustrates original vials inserted into a smart narcotics case with narcotics indicators, according to some embodiments of the present disclosure.

Referring now to FIG. 9B, original vials inserted into a smart narcotics case 900 with narcotics indicators 955 are illustrated. In some embodiments, original vials 930 may be inserted in a smart narcotics case 900, which may trigger an activation of narcotics indicators 955. In some aspects, narcotics indicators 955 may allow for coordination of narcotics between original vials 930 and waste vials. The narcotics indicators 955 may be automatic, wherein the narcotics indicators 955 may detect narcotic type of the original vials 930. For example, each original vial 930 may comprise an identifying mechanism, such as a bar code, QR code, or other technology, which may transmit narcotics type when inserted into a smart narcotics case 900. Once inserted, narcotics indicators 955 for the waste vials may be generated to match the type of narcotics in the original vials 930, which may allow for easy and accurate coordination of narcotics between original vials 930 and waste vials.

Figure 10A:
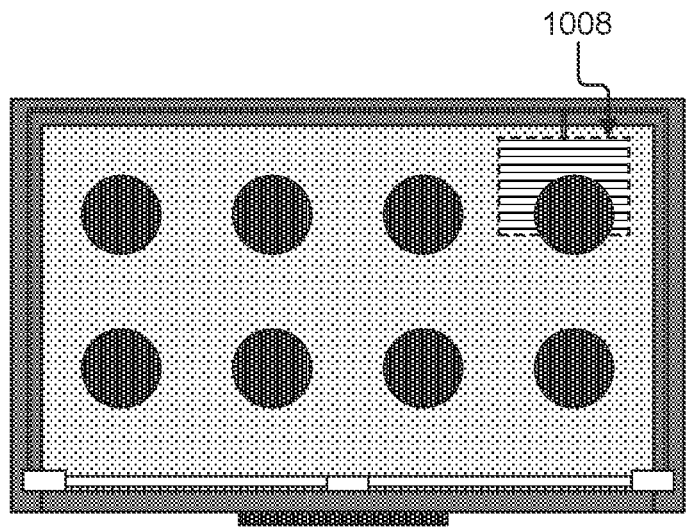
FIG. 10A illustrates an exemplary smart narcotics case with an access sensor, wherein access is not detected, according to some embodiments of the present disclosure.
Figure 10B:
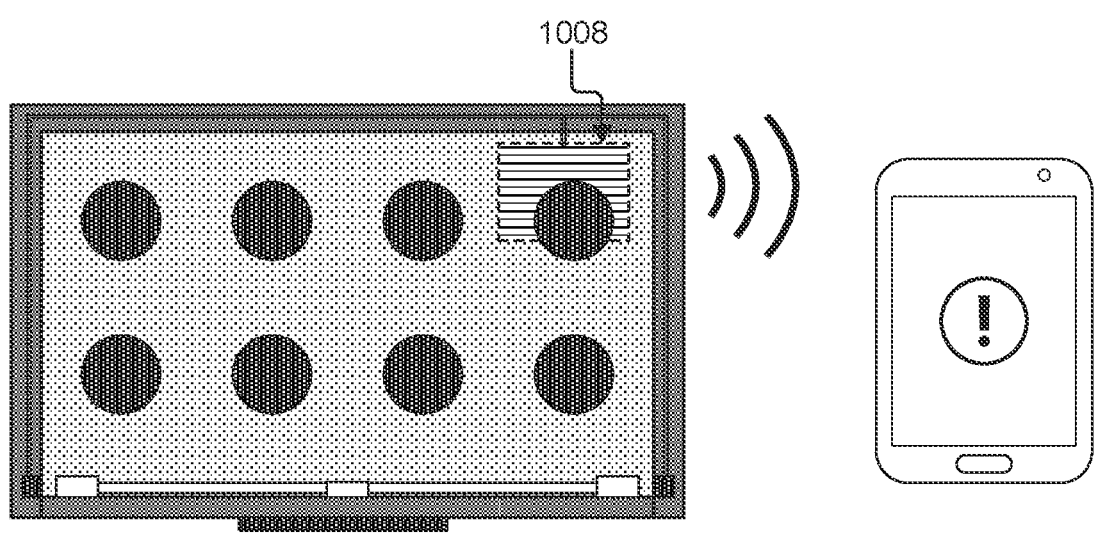
FIG. 10B illustrates an exemplary smart narcotics case with an access sensor, wherein access is detected, according to some embodiments of the present disclosure.

Referring to FIG. 10A, an exemplary smart narcotics case 1000 with an access sensor 1008 is illustrated, wherein access is not detected. Referring now to FIG. 10B, an exemplary smart narcotics case 1000 with an access sensor 1008 is illustrated, wherein access is detected. In some embodiments, an access sensor 1008 may rely on a connection that may only occur when a lid or access panel is in a closed or open state. Once a change in connection is detected, the access sensor 1008 may register access. In some aspects, detected access may trigger a notification, such as to a system or supervisor. In some embodiments, detected access may be logged and stored without a separate notification. Tracking access may provide a layer of security that may further limit risk of tampering or non-permissible use of narcotics.

Referring now FIG. 11A, a perspective view of a self-locking cover 1110 with stopper is illustrated. Referring now to FIG. 11B, a side view of a self-locking cover with stopper is illustrated. In some aspects, a self-locking cover 1110 may comprise a stopper that may engage the self-locking cover and allow for access to a vial by a syringe 1160 or other insertion tip. Once the stopper is pushed out of the hole, the self-locking cover 1110 disengages, and the panel is released. The panel blocks access to the vial. In some embodiments, a self-locking cover 1110 may comprise an access indicator 1115, which may be passive or active. For example, a passive access indicator 1115 may comprise a color that may become exposed when the self-locking cover 1110 is disengaged. An active access indicator 1115 may comprise a light. The light may turn on or off or may comprise a range of colors, which may indicate engagement.

Figure 12:
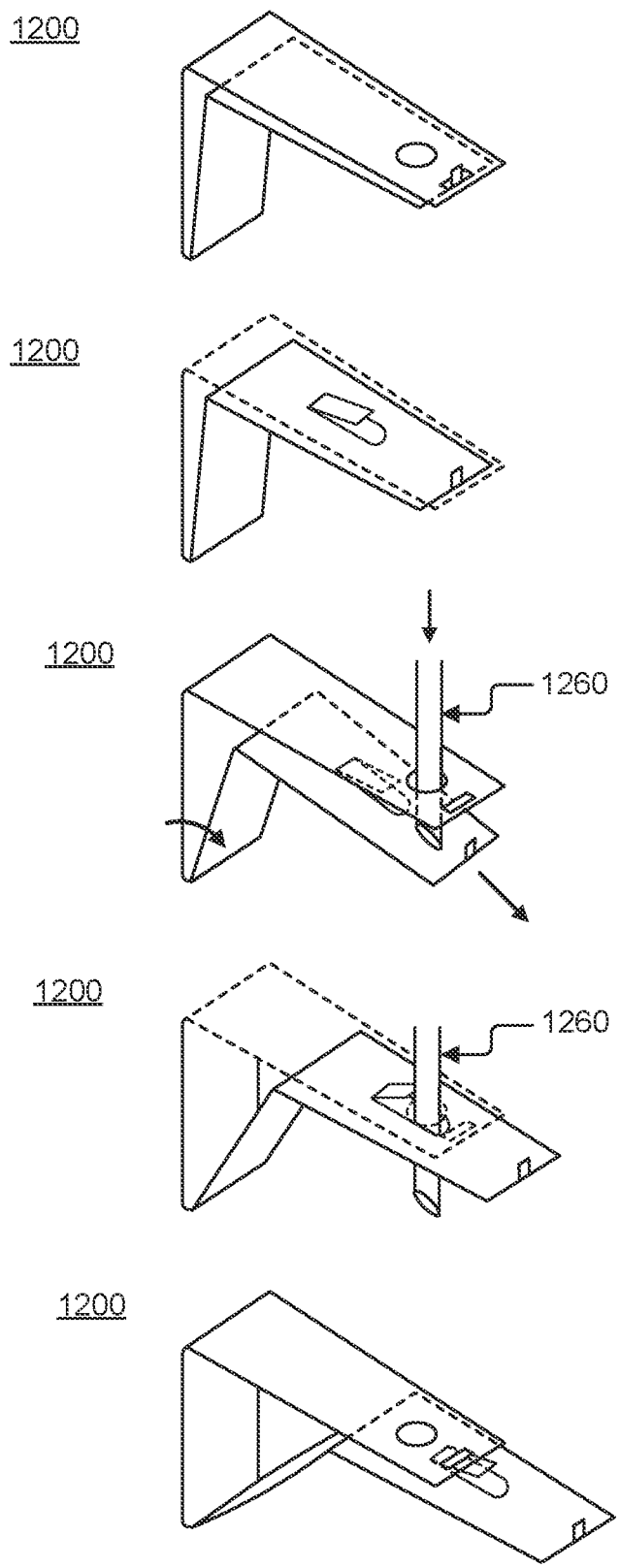
FIG. 12 illustrates a perspective view of an exemplary self-locking cover, according to some embodiments of the present disclosure.

Referring now to FIG. 12, a perspective view of an exemplary self-locking cover 1200 is illustrated. In some aspects, a self-locking cover 1200 may comprise tabs that may engage and disengage as a syringe 1260 is inserted. Once a panel is pushed down by a syringe 1260 or other insertion tip, the portion engaging the self-locking cover 1200 may be disengaged, which may block access from any subsequent attempts. In some embodiments, the self-locking cover 1200 may be incorporated into an insertion panel, such as illustrated in FIG. 4. The self-locking cover 1200 may engage with an exterior that may secure the disengaged panel in place.

Referring now to FIG. 13A, a perspective view of an exemplary self-locking cover with spring clip is illustrated. Referring now to FIG. 13B, a side view of an exemplary self-locking cover with spring clip is illustrated. Referring now to FIG. 13C, a top down view of an exemplary self-locking cover with spring clip is illustrated. In some embodiments, a self-locking cover 1300 may comprise a spring clip mechanism that may be disengaged when a syringe 1360 or other insertion tip is inserted into self-locking cover 1300. In some implementations, the self-locking cover 1300 may comprise a secondary hole that may accept and guide the syringe 1360. In some aspects, pushing the syringe 1360 into the vial may cause a panel to shift into place and cover an insertion site. In some embodiments, the panel may comprise a color that may indicate disengagement.

Referring now to FIG. 14, a side view of an exemplary self-locking cover 1400 with a spring mechanism 1414 is illustrated. In some aspects, a flexible panel 1412 may be blocked by a partial wall, and a spring may be engaged. Pushing a syringe 1460 may push the flexible panel 1412 beyond the partial wall, allowing the spring 1414 to disengage. Once disengaged, a blocking panel or piece may shift into place covering the insertion hole. In some embodiments, a self-locking cover 1400 may comprise a lid and locking mechanism, such as where the self-locking cover 1400 may be attached or tightened onto a vial. In some implementations, the self-locking cover 1400 may be a component of a smart narcotics case, wherein the self-locking cover 1400 may control access to vials through the smart narcotics case, such as through an insertion panel.

Figure 15:
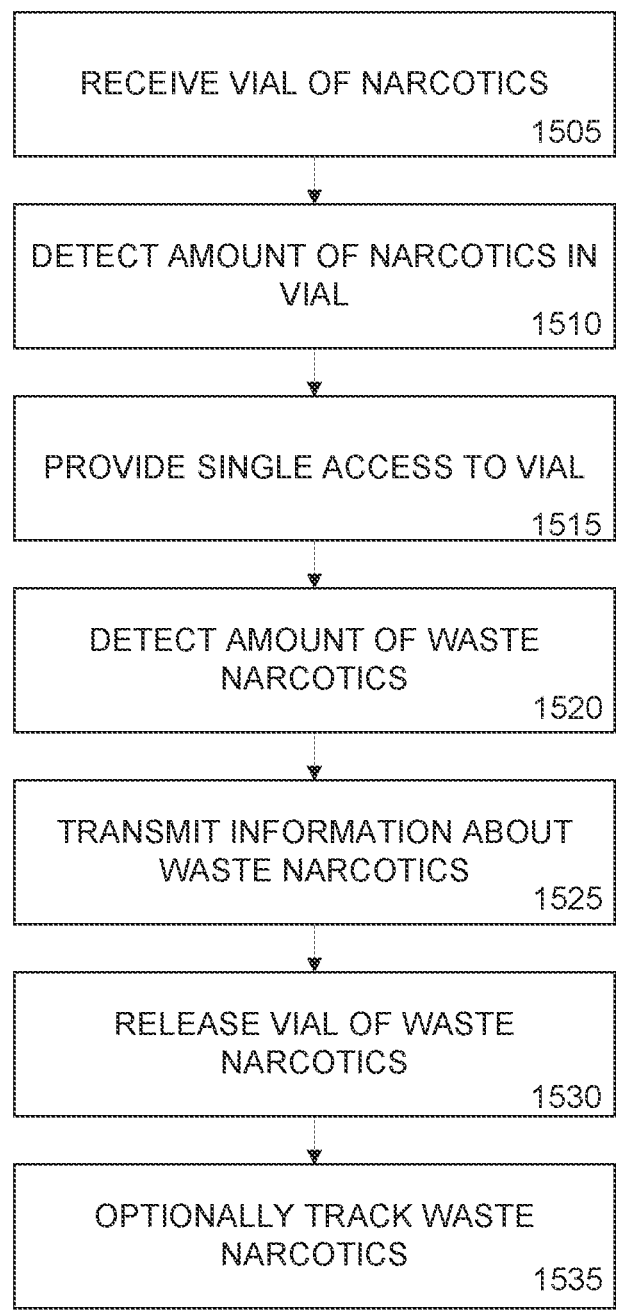
FIG. 15 illustrates an exemplary method for tracking waste, according to some embodiments of the present disclosure.

Referring now to FIG. 15, an exemplary method for tracking waste is illustrated. At 1505, a vial of narcotics may be received, such as into a smart narcotics case. At 1510, an amount of narcotics in the vial may be detected, such as through a volume sensor or scale. At 1515, single access may be provided to the vial. At 1520, an amount of waste narcotics may be detected, which may comprise any remaining narcotics in the vial. At 1525, information about the waste narcotics may be transmitted. At 1530, the vial of waste narcotics may be released. In some aspects, at 1535, the waste narcotics may be tracked.

Conclusion

A number of embodiments of the present disclosure have been described. While this specification contains many specific implementation details, these should not be construed as limitations on the scope of any disclosures or of what may be claimed, but rather as descriptions of features specific to particular embodiments of the present disclosure.

Certain features that are described in this specification in the context of separate embodiments can also be implemented in combination in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

Moreover, the separation of various system components in the embodiments described above should not be understood as requiring such separation in all embodiments, and it should be understood that the described program components and systems can generally be integrated together in a single product or packaged into multiple products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multi-tasking and parallel processing may be advantageous. Nevertheless, it will be understood that various modifications may be made without departing from the spirit and scope of the claimed disclosure.

What is claimed is:

1. A method for tracking narcotics waste, the method comprising:
   receiving a first vial of narcotics into a smart narcotics case;
   detecting a first amount of narcotics in the first vial;
   providing single access to narcotics in the first vial;
   withdrawing a second amount of narcotics from the first vial, wherein the second amount comprises at least a portion of the first amount;
   detecting a waste amount of narcotics remaining in the first vial;
   transmitting data about the waste amount of narcotics, wherein the data comprises at least the waste amount of narcotics; and
   releasing the first vial of narcotics.

2. The method of claim 1, wherein the narcotics comprises a liquid and access to the narcotics is limited to a syringe.

3. The method of claim 1, wherein the narcotics comprises a capsule, tablet, or solid form.

4. The method of claim 1, further comprising tracking the waste amount of narcotics, wherein tracking determines at least a current location of the vial.

5. The method of claim 1, wherein the smart narcotics case comprises a wireless mechanism, and wherein transmission of data occurs wirelessly.

6. The method of claim 1, further comprising detecting a narcotics type, wherein the data comprises the narcotics type.

7. The method of claim 1, wherein the first vial comprises:
   a container portion configured to contain narcotics, and
   a self-locking cover configured to allow for single access to the narcotics.

8. The method of claim 7, wherein the smart narcotics case comprises:
   a base comprising at least one recess, wherein the at least one recess is configured to accept the first vial, and
   a lid comprising at least one opening, wherein the at least one opening is located proximate to the self-locking cover, allowing single access to the narcotics.

\* \* \* \* \*